(12) United States Patent
Kunz et al.

(10) Patent No.: US 9,512,157 B2
(45) Date of Patent: Dec. 6, 2016

(54) METHODS FOR PREPARING RUTHENIUM CARBENE COMPLEXES AND PRECURSORS THERETO

(71) Applicant: ELEVANCE RENEWABLE SCIENCES, INC., Woodridge, IL (US)

(72) Inventors: Linda A. Kunz, Naperville, IL (US); Steven A. Cohen, Naperville, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 229 days.

(21) Appl. No.: 14/087,954

(22) Filed: Nov. 22, 2013

(65) Prior Publication Data

US 2014/0155621 A1 Jun. 5, 2014

Related U.S. Application Data

(60) Provisional application No. 61/731,815, filed on Nov. 30, 2012.

(51) Int. Cl.
C07F 15/00 (2006.01)
B01J 31/22 (2006.01)

(52) U.S. Cl.
CPC ........ *C07F 15/0046* (2013.01); *B01J 31/2265* (2013.01); *B01J 31/2295* (2013.01); *B01J 2231/543* (2013.01); *B01J 2531/821* (2013.01)

(58) Field of Classification Search
CPC .................................................. C07F 15/0046
See application file for complete search history.

(56) References Cited

U.S. PATENT DOCUMENTS

| | | |
|---|---|---|
| 7,329,758 B1 | 2/2008 | Grubbs et al. |
| 2013/0096313 A1 | 4/2013 | Kunz et al. |
| 2013/0096314 A1 | 4/2013 | Kunz et al. |

FOREIGN PATENT DOCUMENTS

| | | |
|---|---|---|
| WO | WO 2013/055644 A2 | 4/2013 |

OTHER PUBLICATIONS

Albers et al. "14. (n4-1,5-cyclooctadiene)ruthenium(II) Complexes" Inorganic Syntheses, vol. 26, 1989, pp. 68-77.*
Chatani et al. "Product Class 9: Organometallic Complexes of Ruthenium" Science of Synthesis, 2002, pp. 931-972.*
Albers, Michel O. et al., "(η⁴-1,5-Cyclooctadiene)Ruthenium(II) Complexes," Inorganic Syntheses, vol. 26, © 1989 by Inorganic Syntheses, Inc., pp. 68-77.
Bernardis, Francesco L. et al., "A review of methods of separation of the platinum-group metals through their chloro-complexes," Reactive & Functional Polymers, vol. 65, 2005, pp. 205-217.
Chakravarty, Akhil R. et al., "New Preparations and Molecular Structures of cis-MCl$_{22}$(Ph$_2$PCH$_2$PPh$_2$)$_2$, M=Ru, Os and trans-RuCl$_2$(Ph$_2$PCH$_2$PPh$_2$)$_2$," Inorganica Chimica Acta, vol. 84, 1984, pp. 179-185.
Chatani, N., "Product Class 8: Organometallic Complexes of Ruthenium," Science of Synthesis, Category 1—Organometallics, vol. 1, Jan. 2002, pp. 931-972.
Deloume, Par Jean-Pierre et al., "Nouvelle Détermination de la Structure Cristalline du μ-Oxo-bis[pentachlororuthénate-(IV)] de Potassium, K$_4$[Ru$_2$Cl$_{10}$O], et Affinement de la Structure de l'Hexachlororuthenate de Potassium, K$_2$[RuCl$_6$]," Acta. Cryst., vol. B35, 1979, pp. 558-561.
Emel'yanov, V.A. et al., "Crystal Structure of Ammonium Pentachloro-Aquaruthenate(III) (NH$_4$)$_2$[Ru(H$_2$O)Cl$_5$]," Journal of Structural Chemistry, vol. 49, No. 3, 2008, pp. 566-569, translated from Zhurnal Strkturnoi Khimii, vol. 49, No. 3, May-Jun. 2008, pp. 585-588.
Frosin, K.-M. et al., "The Reduction of Hydrated Ruthenium (III) Chloride with Zinc in the Presence of Cyclooctadiene: Molecular Structure of Ru(C$_8$H$_{10}$)(C$_8$H$_{12}$) and Isolation and X-ray Structural Characterization of Ru$_2$Cl$_4$(C$_8$H$_{12}$)$_2$, RuH(C$_8$H$_{11}$)(C$_6$H$_6$) and Ru$_3$Cl$_3$(OCH$_3$)(C$_8$H$_{12}$)$_3$," Inorganica Chimica Acta, vol. 167, 1990, pp. 83-89. Hallman, P.S. et al., "Tetrakis (Triphenylphosphine) Dichlororuthenium(II) and Tris(Triphenylphosphine)-Dichlororuthenium(II)," Inorganic Syntheses, vol. XII, © 1970, McGraw-Hill Book Company, Inc., pp. 237-240.
Lobana, Tarlok S. et al., "Thiosemicarbazonates of ruthenium(II): Crystal structures of [bis(diphenylphosphino)butane]-[bis(pyridine-2-carbaldehydethiosemicarbazonato)] ruthenium(II) and [bis(triphenylphosphine)][bis(benzyldehydethiosemicarbazonato)] ruthenium(II)," Polyhedron, vol. 25, 2006, pp. 2897-2903.
Scholl, Matthias et al., "Synthesis and Activity of a New Generation of Ruthenium-Based Olefin Metathesis Catalysts Coordinated with 1,3-Dimesityl-4,5-dihydroimidazol-2-ylidene Ligands§," Organic Letters, vol. 1, No. 6, 1999, pp. 953-956.
Schwab, Peter et al., "Synthesis and Applications of RuCl$_2$(=CHR)(PR$_3$)$_2$: The Influence of the Alkylidene Moiety on Metathesis Activity," J. Am. Chem. Soc., vol. 118, 1996, pp. 100-110.
Stephenson, T.A. et al., "New Complexes of Ruthenium (II) and (III) with Triphenylphosphine, Triphenylarsine, Trichlorostannate, Pyridine and Other Ligands," J. Inorg. Chem., vol. 28, 1966, pp. 945-956.
Wilhelm, Thomas E. et al., "Reactivity of Ru(H)(H$_2$)Cl(PCy$_3$)$_2$ with Propargyl and Vinyl Chlorides: New Methodology to Give Metathesis-Active Ruthenium Carbenes," Organometallics, vol. 16, No. 18, Sep. 2, 1997, pp. 3867-3869.
International Search Report and Written Opinion of the International Searching Authority for International Application No. PCT/US2013/071724, dated Feb. 27, 2014, 18 pages.

* cited by examiner

*Primary Examiner* — Joseph Kosack
(74) *Attorney, Agent, or Firm* — Robert S. Dailey

(57) ABSTRACT

Methods of preparing ruthenium carbene complex precursors are disclosed herein. In some embodiments, the methods include reacting a ruthenium refinery salt with an L-type ligand and a reducing agent to form the ruthenium carbene complex precursor. Methods of preparing a ruthenium vinylcarbene complex are also disclosed. In some embodiments, preparing a ruthenium carbene complex includes converting a ruthenium carbene complex precursor into a ruthenium carbene complex having a structure $(PR^1R^2R^3)_2 Cl_2Ru=CH-R^4$, wherein $R^1$, $R^2$, $R^3$, and $R^4$ are defined herein.

24 Claims, 6 Drawing Sheets

METHODS FOR PREPARING RUTHENIUM CARBENE COMPLEXES AND PRECURSORS THERETO

CROSS-REFERENCE TO RELATED APPLICATIONS

The present application claims the benefit of priority of U.S. Provisional Patent Application No. 61/731,815, filed Nov. 30, 2012, which is hereby incorporated by reference in its entirety as though fully set forth herein.

TECHNICAL FIELD

The present teachings relate generally to ruthenium carbene complex precursors and preparations thereof, as well as to the use of such precursors in the preparation of ruthenium carbene complexes.

BACKGROUND

With the development of new, relatively air-stable transition metal carbene complex catalysts, particularly ones exhibiting increased tolerance towards common organic functional groups, the olefin metathesis reaction has established itself as one of the most powerful reactions in the synthetic preparation of alkenes.

Ruthenium carbene complexes, for example, the "first-generation" and "second generation" Grubbs-type catalysts, can be used as catalysts for olefin metathesis. The polymeric di-μ-chloro($\eta^4$-1,5-cyclooctadiene)ruthenium(II), represented herein as $[RuCl_2(COD)]_x$, and the monomeric tris(triphenylphosphine)ruthenium(II) chloride, represented herein as $RuCl_2(PPh_3)_3$, can be used as precursors in the synthesis of certain ruthenium carbene complexes.

As shown in FIG. 1, $[RuCl_2(COD)]_x$ (*Inorganic Syntheses*, 1989, 29, 68-77) and $RuCl_2(PPh_3)_3$ (*Inorganic Syntheses*, 1970, 12, 237-240) are typically prepared starting from $RuCl_3 \cdot nH_2O$. The hydrated ruthenium trichloride is itself prepared starting from ruthenium refinery salts (e.g., salts of ruthenium-halo complexes produced in the refining of natural platinum group metal deposits and recycled platinum group metals). However, since the ruthenium refinery salts are first reduced to ruthenium metal, which in turn is then oxidized to Ru(III), the preparations of $[RuCl_2(COD)]_x$ and $RuCl_2(PPh_3)_3$ via the intermediacy of ruthenium trichloride can be costly and inefficient.

A more efficient and less costly preparation of $[RuCl_2(COD)]_x$, $RuCl_2(PPh_3)_3$, and analogous $MX_2L_q$ ruthenium carbene complex precursors from ruthenium refinery salts, particularly one that does not require the intermediacy of ruthenium metal and/or hydrated ruthenium trichloride, may be desirable.

SUMMARY

The scope of the present invention is defined solely by the appended claims, and is not affected to any degree by the statements within this summary.

By way of introduction, a first method for preparing a ruthenium carbene complex precursor in accordance with the present teachings includes reacting a ruthenium refinery salt with an L-type ligand and a reducing agent to form the ruthenium carbene complex precursor.

A second method for preparing a ruthenium carbene complex precursor in accordance with the present teachings includes reacting a ruthenium refinery salt with an L-type ligand and a reducing agent to form the ruthenium carbene complex precursor, wherein the L-type ligand includes cyclooctadiene (COD) and/or a phosphorus-containing material having a structure $PR^1R^2R^3$. The ruthenium refinery salt includes a material selected from the group consisting of $(NH_4)_2RuCl_5$, $(NH_4)_2RuCl_5 \cdot H_2O$, polyhydrated $(NH_4)_2RuCl_5$, $(NH_4)_4[Ru_2OCl_{10}]$, and combinations thereof. The reducing agent includes a metal selected from the group consisting of Group 7 elements, Group 8 elements, Group 9 elements, Group 10 elements, Group 11 elements, and combinations thereof. The ruthenium carbene complex precursor includes a compound having a structure $[RuCl_2(COD)]_x$ and/or a compound having a structure $RuCl_2(PR^1R^2R^3)_3$, wherein (a) x is an integer value of 1 or more; (b) $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof; and (c) covalent bonds may optionally exist between two or more of $R^1$, $R^2$, and $R^3$ and/or two of $R^1$, $R^2$, and $R^3$ taken together may optionally form a ring with phosphorus.

A first method for preparing a ruthenium vinylcarbene complex in accordance with the present teachings includes (a) converting a ruthenium carbene complex precursor prepared according to a method described above into a ruthenium hydrido halide complex; and (b) reacting the ruthenium hydrido halide complex with a propargyl halide to form the ruthenium vinylcarbene complex.

A method for preparing a ruthenium carbene complex in accordance with the present teachings includes converting a ruthenium carbene complex precursor prepared according to a method described above into a ruthenium carbene complex having a structure $(PR^1R^2R^3)_2X^1X^2Ru=CH-R^4$, wherein (a) $X^1$ and $X^2$ are halogen atoms that are each independently selected from the group consisting of F, Cl, Br, and I; (b) $R^1$, $R^2$, $R^3$, and $R^4$ are alike or different, and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof; and (c) covalent bonds may optionally exist between two or more of $R^1$, $R^2$, and $R^3$ and/or two of $R^1$, $R^2$, and $R^3$ taken together may optionally form a ring with phosphorus.

A method of preparing a product that comprises $[RuCl_2(COD)]_x$, in accordance with the present teachings includes reacting a ruthenium refinery salt with cyclooctadiene and a reducing agent in an alcoholic solvent under reflux conditions to form the product, wherein (a) x is an integer value of 1 or more; (b) the ruthenium refinery salt includes a material selected from the group consisting of $(NH_4)_2RuCl_5$, $(NH_4)_2RuCl_5 \cdot H_2O$, polyhydrated $(NH_4)_2RuCl_5$, $(NH_4)_4[Ru_2OCl_{10}]$, and combinations thereof; and (c) the reducing agent includes a metal selected from the group consisting of Group 7 elements, Group 8 elements, Group 9 elements, Group 10 elements, Group 11 elements, and combinations thereof.

Other aspects and embodiments of the present disclosure are set forth in the Detailed Description, found below.

DETAILED DESCRIPTION

Figure 1:
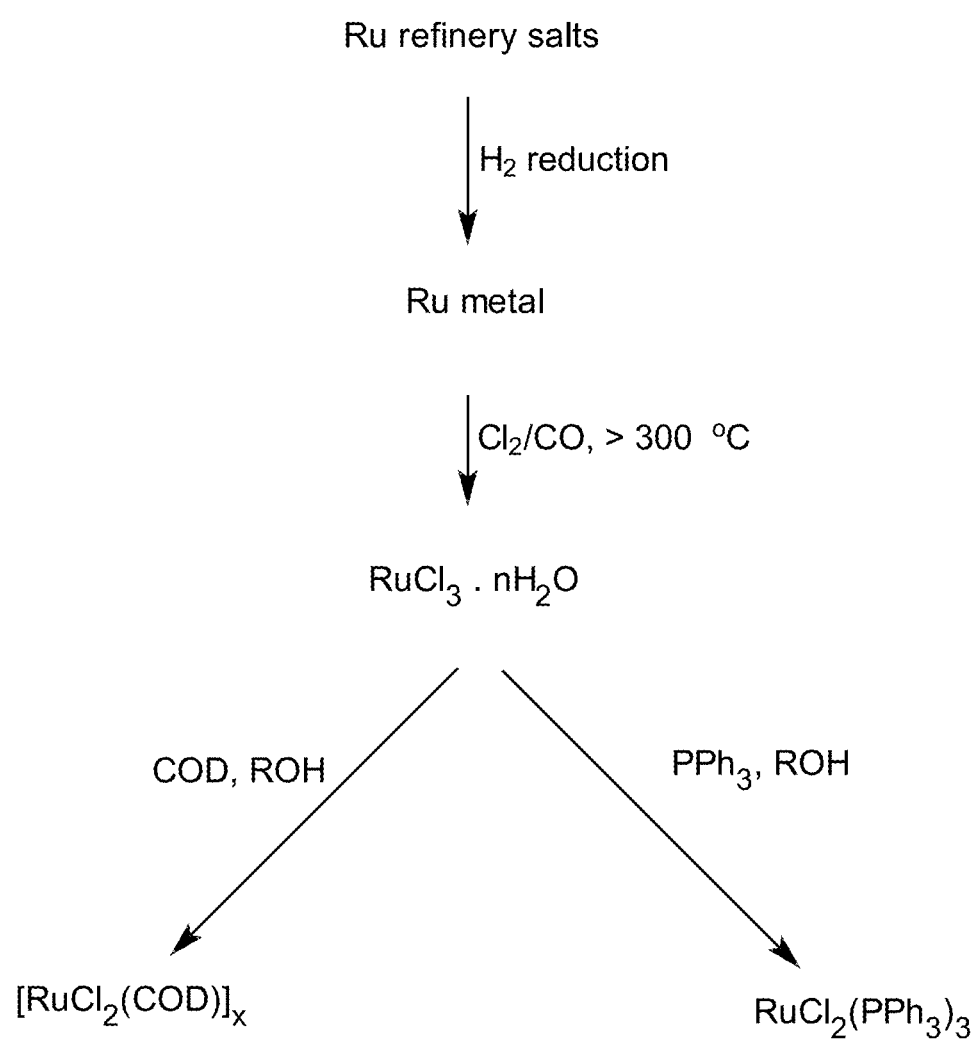
FIG. 1 shows a synthetic scheme for converting ruthenium refinery salts to $[RuCl_2(COD)]_x$ and $RuCl_2(PPh_3)_3$ by conventional methodologies.
Figure 2:
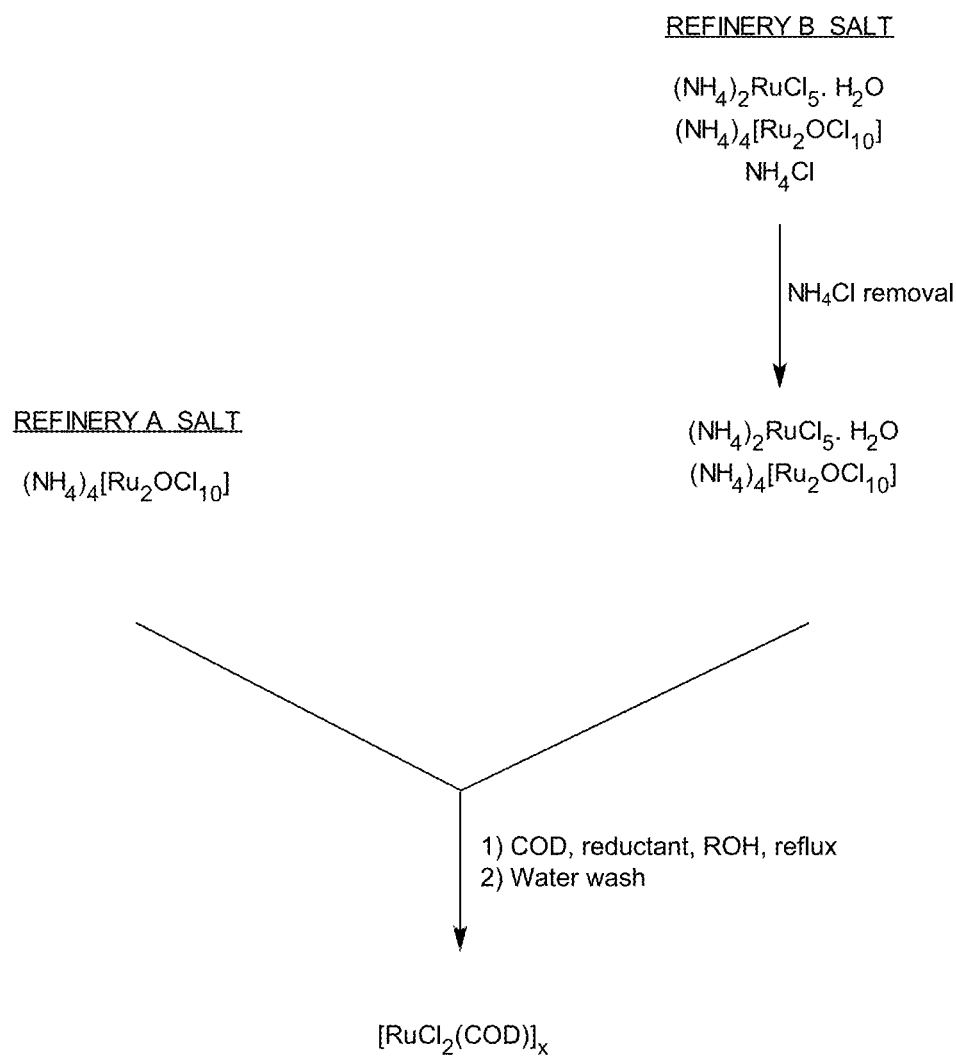
FIG. 2 shows a synthetic scheme for converting ruthenium refinery salts to [RuCl$_2$(COD)]$_x$ in accordance with the present teachings.
Figure 4:
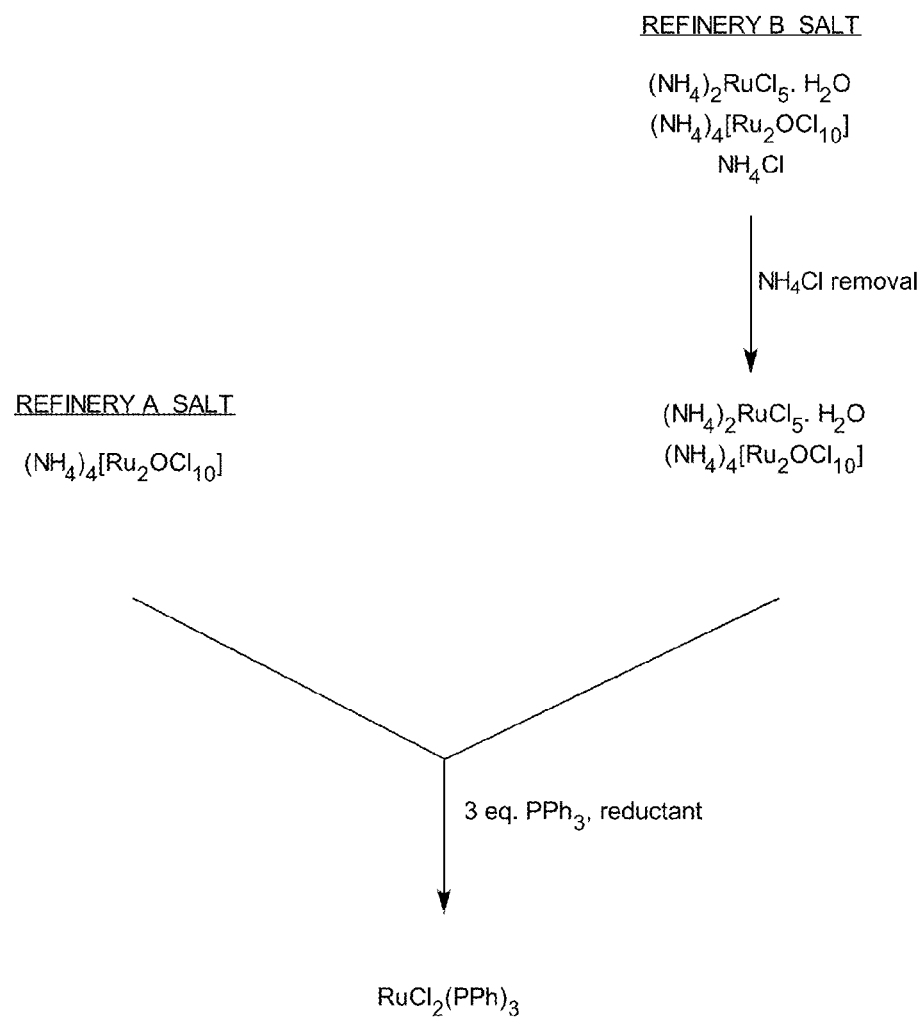
FIG. 4 shows a synthetic scheme for converting ruthenium refinery salts to RuCl$_2$(PPh$_3$)$_3$ in accordance with the present teachings.

A facile synthetic route to ruthenium carbene complex metathesis catalyst precursors, such as [RuCl$_2$(COD)]$_x$, RuCl$_2$(PPh$_3$)$_3$, and analogous MX$_2$L$_q$ complexes (e.g., where q is an integer from 1 through 4), is, among other embodiments, described herein. As shown in FIGS. 2 and 4, the disclosed route starts from ruthenium refinery salts and does not require any conversion of these salts to ruthenium metal or subsequent oxidation of ruthenium metal to hydrated RuCl$_3$, which are two of the principal drawbacks associated with the conventional synthetic preparations of [RuCl$_2$(COD)]$_x$, RuCl$_2$(PPh$_3$)$_3$, and analogous complexes.

Throughout this description and in the appended claims, the following definitions are to be understood. Terms not expressly defined shall have the meaning that such terms would have to ordinarily skilled artisans in the field(s) relevant to this disclosure.

The phrase "ruthenium carbene complex precursor" refers generally to any ruthenium complex useful in the preparation of various ruthenium reagents and/or catalyst compositions, including but not limited to carbene complexes.

The phrase "ruthenium refinery salt" refers generally to a ruthenium- and halogen-containing material. It is to be understood that a "ruthenium refinery salt" as defined herein may further comprise additional elements besides ruthenium and halogen, including but not limited to oxygen. Representative examples of "ruthenium refinery salts" include but are not limited to materials obtained from—or substantially chemically equivalent to what could otherwise be obtained from—the processing of a natural platinum group metal (PGM) deposit, as well as materials obtained from alternative chemical sources (e.g., ammoniated ruthenium oxychloride a.k.a. ruthenium red, etc.) and/or from recovery and/or reclamation processing of a ruthenium-containing material used in a prior chemical reaction. In some embodiments, a "ruthenium refinery salt" is obtained from a natural PGM deposit by a technique as described in *Reactive & Functional Polymers*, 2005, 65, 205-217.

The phrase "L-type ligand" refers to a two-electron neutral ligand. Representative examples of an "L-type ligand" for use in accordance with the present teachings include but are not limited to olefins, phosphines, phosphites, amines, carbon monoxide (CO), nitrogen (N$_2$), and the like, and combinations thereof.

The phrase "reducing agent" refers generically to any species capable of reducing another species while itself being oxidized. As used herein, it is to be understood that this capability may or may not be an actual mechanistic factor involved in the direct conversion of a ruthenium refinery salt to a ruthenium carbene complex precursor. In other words, the mechanism by which the reducing agent participates in the conversion of a ruthenium refinery salt to a ruthenium carbene complex precursor may or may not involve oxidation and/or reduction.

The term "olefin" refers to a hydrocarbon compound containing at least one carbon-carbon double bond. As used herein, the term "olefin" encompasses straight, branched, and/or cyclic hydrocarbons having only one carbon-carbon double bond (e.g., monoenes) as well as more than one carbon-carbon double bond (e.g., dienes, trienes, etc.). In some embodiments, the olefin is functionalized.

The term "functionalized" as used in reference to an olefin refers to the presence of one or more heteroatoms, wherein the heteroatom is an atom other than carbon and hydrogen. In some embodiments, the heteroatom constitutes one atom of a polyatomic functional group with representative functional groups including but not limited to carboxylic acids, carboxylic esters, ketones, aldehydes, anhydrides, sulfur-containing groups, phosphorus-containing groups, amides, imides, N-containing heterocycles, aromatic N-containing heterocycles, salts thereof, and the like, and combinations thereof.

It is to be understood that elements and features of the various representative embodiments described below may be combined in different ways to produce new embodiments that likewise fall within the scope of the present teachings.

By way of general introduction, a method for preparing a ruthenium carbene complex precursor in accordance with the present teachings comprises reacting a ruthenium refinery salt with an L-type ligand and a reducing agent to form the ruthenium carbene complex precursor in a direct one-step conversion. This one-step process complements related two-step processes that are described in United States Published Patent Application Nos. 2013/0096313 and 2013/0096314, each of which is hereby incorporated by reference as though fully set forth herein, except that in the event of any inconsistent disclosure or definition from the present specification, the disclosure or definition herein shall be deemed to prevail.

By way of illustration, and as further described below, the ruthenium carbene complex precursor [RuCl$_2$(COD)]$_x$ was synthesized in high yield (e.g., 97-98%) by a direct one-step conversion starting from a ruthenium refinery salt and a reducing agent in an alcohol solvent. Although the methodology described herein has been demonstrated using ruthenium refinery salts obtained from two different refineries (referred to herein generically as Refineries A and B), it is to be understood that methods in accordance with the present teachings are not restricted to specific ruthenium feedstocks but can be applied with ruthenium salts obtained from other refineries as well.

In some embodiments, the L-type ligand is selected from the group consisting of olefins, phosphines, phosphites, amines, CO, N$_2$, and combinations thereof. In some embodiments, the L-type ligand is selected from the group consisting of olefins, phosphines, and a combination thereof.

In some embodiments, the L-type ligand comprises an olefin. In some embodiments, the olefin is selected from the group consisting of monoenes, dienes, trienes, and the like, all stereoisomers thereof, and combinations thereof. In some embodiments, the olefin is acyclic. In some embodiments, the olefin comprises an acyclic C$_6$ or greater monoene. In some embodiments, the olefin comprises an acyclic diene with representative acyclic dienes including but not limited to 1,5-hexadiene, 2,6-octadiene, and the like, and combinations thereof. In some embodiments, the olefin is cyclic. In some embodiments, the olefin comprises a cyclic diene with representative cyclic dienes including but not limited to cyclopentadiene, cyclohexadiene, cycloheptadiene, cyclooctadiene, cyclononadiene, cyclodecadiene, cycloundecadiene, cyclododecadiene, paramenthadiene, phellandrene, norbornadiene, terpinene, limonene, and the like, and combinations thereof. In some embodiments, the olefin comprises an acyclic triene. In some embodiments, the olefin comprises a cyclic triene with a representative cyclic triene including but not limited to cyclododecatriene. In some embodiments, the olefin is aromatic with representative aromatic olefins including but not limited to cyclopentadienyl, benzene, toluene, o-xylene, m-xylene, p-xylene, mesitylene, and the like, and combinations thereof.

In some embodiments, about two molar equivalents of a cyclic olefin per ruthenium in the ruthenium refinery salt are used to form a ruthenium carbene complex precursor in accordance with the present teachings. In some embodiments, about two molar equivalents of cyclooctadiene are reacted with a ruthenium refinery salt and a reducing agent to form a ruthenium carbene complex precursor in accordance with the present teachings. In some embodiments, the olefin (e.g., cyclooctadiene) is reacted with the ruthenium refinery salt and the reducing agent in an alcoholic solvent which, in some embodiments, can further serve as a reducing agent. In some embodiments, the cyclooctadiene reacted with the ruthenium refinery salt and the reducing agent comprises cis, cis-1,5-cyclooctadiene. In some embodiments, the cyclooctadiene comprises cis, cis-1,5-cyclooctadiene, and the reacting comprises refluxing the ruthenium refinery salt, about 2 equivalents of cis, cis-1,5-cyclooctadiene, and about 3 equivalents of a reducing agent in an aliphatic alcoholic solvent. In some embodiments, the reducing agent comprises $FeCl_2$ and the reaction of the ruthenium refinery salt with cis, cis-1,5-cyclooctadiene and the reducing agent to form a ruthenium carbene complex precursor is conducted in ethanol.

In some embodiments, the L-type ligand comprises a phosphorus-containing material (e.g., phosphines, phosphites, and the like, and combinations thereof). In some embodiments, the phosphorus-containing material comprises a structure $PR^1R^2R^3$, wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted arylyoxy, substituted or unsubstituted $C_1$-$C_{10}$ alkoxy, and combinations thereof. In some embodiments, covalent bonds may optionally exist between two or more of $R^1$, $R^2$, and $R^3$. In some embodiments, two of $R^1$, $R^2$, and $R^3$ taken together may optionally form a ring with phosphorus. In some embodiments, one or more of $R^1$, $R^2$, and $R^3$ comprises phenyl. In some embodiments, each of $R^1$, $R^2$, and $R^3$ comprises phenyl. In some embodiments, one or more of $R^1$, $R^2$, and $R^3$ comprises cycloalkyl (e.g., cyclohexyl). In some embodiments, each of $R^1$, $R^2$, and $R^3$ comprises cycloalkyl (e.g., cyclohexyl). In some embodiments, the phosphorus-containing material comprises a phosphine. In some embodiments, the phosphine comprises a trialkyl phosphine. In some embodiments, the phosphine comprises triphenyl phosphine. In some embodiments, the phosphorus-containing material comprises a phosphite.

In some embodiments, the ruthenium refinery salt is reacted with about three equivalents of a phosphorus-containing material (e.g., a phosphine) and a reducing agent in accordance with the present teachings to form a ruthenium carbene complex precursor comprising a structure $RuCl_2(PR^1R^2R^3)_3$, wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. In some embodiments, covalent bonds may optionally exist between two or more of $R^1$, $R^2$, and $R^3$. In some embodiments, two of $R^1$, $R^2$, and $R^3$ taken together may optionally form a ring with phosphorus.

The chemical composition of a particular ruthenium refinery salt for use in accordance with the present teachings can differ according to the specific process used to generate it, the refinery that produced it, the specific lot no. and/or batch from within a given refinery, and/or the exact methodology used to separate the ruthenium from a natural PGM deposit or recovered PGM source. Moreover, it is to be understood that a ruthenium refinery salt in accordance with the present teachings can include one or more impurities—including but not limited to Ru metal, $NH_4Cl$, and the like, and combinations thereof—that are either removed, either partially or completely, prior to reacting the ruthenium refinery salt with the L-type ligand and reducing agent, or else carried along, either in whole or in part, for the reaction.

In some embodiments, a ruthenium refinery salt in accordance with the present teachings comprises one or a plurality of halide ligands and/or one or a plurality of cations. In some embodiments, the ruthenium refinery salt comprises one or a plurality of ammonium cations. In some embodiments, the ruthenium refinery salt comprises one or a plurality of different cations (e.g., alkali metal cations, including but not limited to potassium and sodium, etc.) instead of or in addition to one or a plurality of ammonium cations. In some embodiments, a ruthenium refinery salt in accordance with the present teachings comprises one or a plurality of chloride ligands and/or one or a plurality of ammonium cations. In some embodiments, a ruthenium refinery salt for use in accordance with the present teachings is one produced by Refinery A. In some embodiments, the ruthenium refinery salt is one produced by Refinery B. In some embodiments, the ruthenium refinery salt is a combination of a material produced by Refinery A and a material produced by Refinery B.

As further described below in Examples 1, 2, and 18, x-ray powder diffraction (XRD) analysis of representative ruthenium refinery salts obtained from Refinery A and Refinery B was performed. As shown in Example 2, the XRD analysis of a representative ruthenium refinery salt obtained from Refinery B revealed the following composition: $(NH_4)_4[Ru_2OCl_{10}]$ (36.4 wt %), $(NH_4)_2RuCl_5 \cdot H_2O$ (13.9 wt %), and $NH_4Cl$ (49.3 wt %). By contrast to the large weight percentage of $NH_4Cl$ impurity identified in the Refinery B sample, an XRD analysis of a representative ruthenium refinery salt from a first lot obtained from Refinery A revealed the following composition, as shown in Example 1: $(NH_4)_4[Ru_2OCl_{10}]$ (96.1 wt %) and Ru metal impurity (3.9 wt %). As shown in Example 18, XRD analysis of representative ruthenium refinery salts from second and third lots also obtained from Refinery A revealed slightly different compositions as compared to the first lot analyzed in Example 1. More specifically, the second and third lots analyzed in Example 18 did not contain ruthenium metal as an impurity.

In some embodiments, a ruthenium refinery salt for use in accordance with the present teachings comprises a material selected from the group consisting of $(NH_4)_2RuCl_5$, $(NH_4)_2RuCl_5 \cdot H_2O$, polyhydrated $(NH_4)_2RuCl_5$, $(NH_4)_4$

[Ru$_2$OCl$_{10}$], and combinations thereof. In some embodiments, a ruthenium refinery salt for use in accordance with the present teachings comprises (NH$_4$)$_4$[Ru$_2$OCl$_{10}$]. In some embodiments, the ruthenium refinery salt further comprises an NH$_4$Cl impurity which, in some embodiments, is residual reagent left over from a ruthenium recovery process (e.g., when NH$_4$Cl is added to solution to precipitate pentachloro ruthenium species).

For some of the embodiments in which a ruthenium refinery salt contains NH$_4$Cl (e.g., some ruthenium refinery salts obtained from Refinery B), it has been found that the reaction with L-type ligand and reducing agent is significantly hindered—a fact that becomes especially apparent upon comparing and contrasting the experimental results shown in Schemes 1 and 2 below for reactions conducted in the presence or absence of additional reducing agent. For example, whereas for some embodiments a ruthenium refinery salt substantially free from NH$_4$Cl (e.g., one obtained from Refinery A) will still react with the L-type ligand cyclooctadiene to give [RuCl$_2$(COD)]$_x$ in about 30% yield even in the absence of added reducing agent (Scheme 1, top), an NH$_4$Cl-contaminated ruthenium refinery salt obtained from Refinery B fails to react in such an absence (Scheme 2, top). Moreover, whereas the un-optimized yield of the conversion using a Refinery A salt can be increased to about 85% simply by the addition of reducing agent (Scheme 1, bottom), the yield of the conversion using a Refinery B salt increases to only about 30% in spite of a similar addition (Scheme 2, bottom).

Scheme 1-Conversion of Ruthenium Refinery Salts from Refinery A

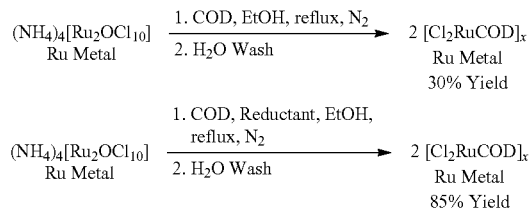

Scheme 2-Conversion of Ruthenium Refinery Salts from Refinery B

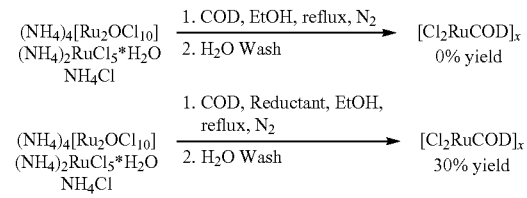

Thus, as further described below, the presence of excess NH$_4$Cl in a ruthenium refinery salt appears to be detrimental to conversions in accordance with the present teachings. Therefore, while neither desiring to be bound by any particular theory nor intending to limit in any measure the scope of the appended claims or their equivalents, it is presently believed that removal of excess NH$_4$Cl prior to reacting the ruthenium refinery salt with the L-type ligand and reducing agent is recommended for some embodiments.

It is to be understood that the reducing agent used in accordance with the present teachings is not restricted, and that all manner of reducing agents are presently contemplated for use. In some embodiments, the reducing agent is organic (e.g., 1,4-CHD, citric acid, ethylene glycol, benzyl alcohol, formic acid, diethylhydroxylamine, etc.). In some embodiments, the reducing agent is inorganic. In some embodiments, the reducing agent comprises a metal which, in some embodiments, is selected from the group consisting of Group 7 elements, Group 8 elements, Group 9 elements, Group 10 elements, Group 11 elements, and combinations thereof. In some embodiments, the reducing agent comprises FeCl$_2$. In some embodiments, the reducing agent comprises a hydrated form of FeCl$_2$ (e.g., monohydrated and/or polyhydrated) including but not limited to FeCl$_2$*4H$_2$O. While neither desiring to be bound by any particular theory nor intending to limit in any measure the scope of the appended claims or their equivalents, it is presently believed that using a hydrated form of the reducing agent (e.g., FeCl$_2$*4H$_2$O) does not appear to have any ill effects on the reaction, such that the yield of the reaction obtained using FeCl$_2$*4H$_2$O as reducing agent is substantially equivalent to that obtained using anhydrous FeCl$_2$. In some embodiments, the reducing agent comprises CoCl$_2$. In some embodiments, the reducing agent comprises a hydrated form of CoCl$_2$ (e.g., monohydrated and/or polyhydrated). In some embodiments, the reducing agent is selected from the group consisting of FeCl$_2$, CoCl$_2$, hydrated forms thereof, and combinations thereof. While neither desiring to be bound by any particular theory nor intending to limit in any measure the scope of the appended claims or their equivalents, it is presently believed that higher yields are observed when FeCl$_2$ is used as a reducing agent as compared to CoCl$_2$ (at least under the conditions tested). Of course, as described above, other reducing agents may also be used.

Figure 6:
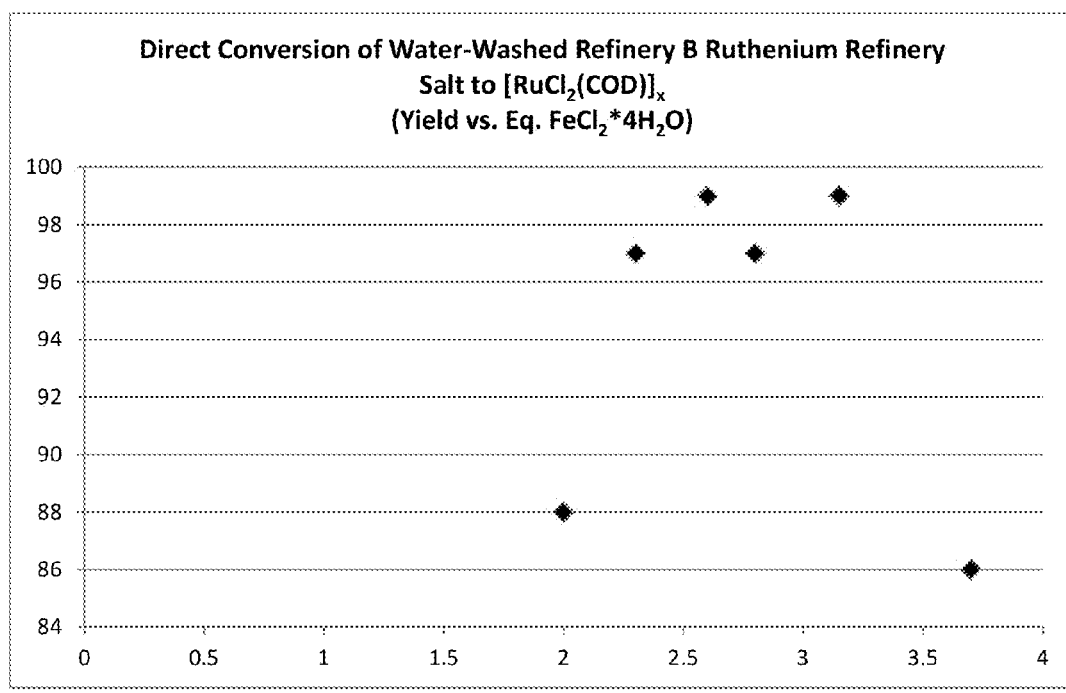
FIG. 6 shows a plot of yield vs. equivalents of FeCl$_2$*4H$_2$O per ruthenium for the direct conversion of water-washed Refinery B ruthenium refinery salt to [RuCl$_2$(COD)]$_x$.

In some embodiments, the reducing agent is present at a loading of at least about 1 molar equivalent per ruthenium in the ruthenium refinery salt. In some embodiments, the reducing agent is present at a loading of at least about 2 molar equivalents per ruthenium in the ruthenium refinery salt. In some embodiments, the reducing agent is present at a loading of at least about 3 molar equivalents per ruthenium in the ruthenium refinery salt. FIG. 6 shows a plot of yield vs. equivalents of FeCl$_2$*4H$_2$O for the direct conversion of a water-washed Refinery B ruthenium refinery salt to [RuCl$_2$(COD)]$_x$. These data are summarized in Table 1 below. As shown by the data in FIG. 6 and Table 1, a catalyst loading from about 2.3 to about 3.2 equivalents of FeCl$_2$*4H$_2$O per Ru center results in nearly quantitative yields of [RuCl$_2$(COD)]$_x$. Thus, it is presently believed that a catalyst loading of about 3 molar equivalents of FeCl$_2$ per Ru is generally optimum for some embodiments although, in some embodiments, it may be advantageous to use fewer molar equivalents, for example to lower the cost.

TABLE 1

Effect of Catalyst Loading on Yield

| Eq. FeCl$_2$ | Yield [RuCl$_2$(COD)]$_x$ |
| --- | --- |
| 2.6 | 99 |
| 2 | 88 |
| 2.3 | 97 |
| 3.15 | 99 |
| 2.8 | 97 |
| 2.6 | 99 |

In some embodiments, the reacting of the ruthenium refinery salt with the L-type ligand and the reducing agent is performed in an alcoholic solvent. While neither desiring to be bound by any particular theory nor intending to limit in any measure the scope of the appended claims or their equivalents, it is presently believed that the alcoholic solvent can act as a reducing agent (e.g., to reduce $Ru^{4+}$ to $Ru^{2+}$) even in the absence of added reducing agent. However, once external reducing agent is added, the solvent can be selected more so on the basis of its boiling point than its reduction capability, with higher boiling solvents enabling higher reaction temperatures, which in turn can be used to force reactions to completion.

Representative alcoholic solvents for use in accordance with the present teachings include but are not limited to aliphatic alcohols (e.g., methanol, ethanol, 1-propanol, isopropanol, 1-butanol, sec-butanol, and the like, and combinations thereof), aromatic alcohols, polyols, and the like, and combinations thereof. In some embodiments, the alcoholic solvent comprises ethanol. In some embodiments, the alcoholic solvent comprises 1-butanol. In some embodiments, the reacting of the ruthenium refinery salt with the L-type ligand and the reducing agent is performed in an alcoholic solvent under reflux conditions. In some embodiments, the reacting of the ruthenium refinery salt with the L-type ligand and the reducing agent comprises a reaction time of at least about 5 hours, in some embodiments at least about 10 hours, in some embodiments at least about 15 hours, in some embodiments at least about 20 hours, and in some embodiments at least about 24 hours.

In some embodiments, the reacting of the ruthenium refinery salt with the L-type ligand and the reducing agent is performed in a non-reactive solvent or in a solvent mixture that comprises one or a plurality of non-reactive solvents and, in some embodiments, is performed under reflux conditions. In some embodiments, the solvent mixture further comprises one or a plurality of alcohols. In some embodiments, the non-reactive solvent comprises an alkane (i.e., a $C_nH_{2n+2}$ saturated hydrocarbon) which, in some embodiments, comprises 6 or more carbon atoms, in some embodiments 7 or more carbon atoms, and in some embodiments 8 or more carbon atoms. In some embodiments, the non-reactive solvent comprises octane. In some embodiments, the solvent mixture further comprises an alcohol which, in some embodiments is branched and, in some embodiments, comprises 2-ethylhexanol.

In some embodiments, the reducing agent comprises $FeCl_2$ and/or a hydrated form thereof, and the L-type ligand comprises a cyclic olefin which, in some embodiments, comprises cyclooctadiene.

In some embodiments, the ruthenium refinery salt is one that is obtained from Refinery A, which—in some embodiments (e.g., lot A in Example 1)—was predetermined by XRD analysis to contain about 96.1 wt % $(NH_4)_4[Ru_2OCl_{10}]$ and about 3.9 wt % Ru metal impurity. In some embodiments, the ruthenium refinery salt is one that is obtained from Refinery A, which, in some embodiments (e.g., lots B and C analyzed in Example 18), does not contain Ru metal impurity. In some embodiments, the ruthenium refinery salt is one that is obtained from Refinery B, which was predetermined by XRD analysis to contain about 36.4 wt % $(NH_4)_4[Ru_2OCl_{10}]$, about 13.9 wt % $(NH_4)_2RuCl_5.H_2O$, and about 49.3 wt % $NH_4Cl$ impurity. As described above, the presence of excess $NH_4Cl$ in a ruthenium refinery salt appears to be detrimental to conversions in accordance with the present teachings and, therefore, removal of excess $NH_4Cl$ prior to reacting the ruthenium refinery salt with an L-type ligand and reducing agent is presently preferred. Thus, in some embodiments, the method in accordance with the present teachings further comprises removing at least a portion of the excess $NH_4Cl$ (if present) from the ruthenium refinery salt prior to reacting the ruthenium refinery salt with the L-type ligand and reducing agent.

Although a substantial amount (e.g., about 80%) of $NH_4Cl$ can be removed by sublimation of the ruthenium refinery salt (e.g., at 175° C.), the yield of $[RuCl_2(COD)]_x$ obtained from direct conversion of a sublimed ruthenium refinery salt is even lower (e.g., less than about 12%) than the yield obtained using an unpurified material (e.g., about 30% under the following conditions: ethanol, 85° C., 3 eq. $FeCl_2*4H_2O$, 24 hours). While neither desiring to be bound by any particular theory nor intending to limit in any measure the scope of the appended claims or their equivalents, it is presently believed that this reduction in yield is a result of a change in the structure of the ruthenium salts at the elevated temperatures of the sublimation.

In some embodiments, at least a portion of the $NH_4Cl$ impurity can be removed by washing—for example, with alcohol (e.g., ethanol, butanol, etc.) and/or water—such as in a flask or a Soxhlet extractor at ambient and/or elevated temperatures. A substantial amount (e.g., about 80%) of $NH_4Cl$ can be removed from a ruthenium refinery salt obtained from Refinery B by washing the material with ethanol, thereby providing a purified material that can be converted to $[RuCl_2(COD)]_x$ in about 79% yield under the following conditions: ethanol, 85° C., 3 eq. $FeCl_2*4H_2O$, 24 hours.

In some embodiments, a substantially quantitative amount (i.e., about 100%) of $NH_4Cl$ can be removed from a ruthenium refinery salt obtained from Refinery B by washing the material with water, thereby providing a purified material that is shown by XRD to be about 100% $(NH_4)_4[Ru_2OCl_{10}]$ and by elemental analysis to contain about 29.6% ruthenium. This purified material can be converted to $[RuCl_2(COD)]_x$ in at least about 98% yield under the following conditions: ethanol, 85° C., 3 eq. $FeCl_2*4H_2O$, 24 hours. Although water washing enables a substantially complete removal of $NH_4Cl$ from a ruthenium refinery salt, in some embodiments the water washing also removes some ruthenium compounds.

In some embodiments, the ruthenium refinery salt used in accordance with the present teachings is a Refinery A sample inasmuch as it does not contain a significant amount of $NH_4Cl$ impurity that would warrant the extra step of its removal. It is to be understood that while the methods described herein have been demonstrated using ruthenium refinery salts from two different refineries—Refinery A and Refinery B—the present teachings can also be applied to ruthenium refinery salts from other refineries as well and without limitation.

In the case of a ruthenium refinery salt obtained from Refinery A, no purification was necessary prior to attempting its reaction with an L-type ligand (e.g., cyclooctadiene) and reducing agent (e.g., $FeCl_2*4H_2O$). In fact, as described above, the conversion proceeds in about 30% yield even in the absence of any added reducing agent (Scheme 1, top). The best yield observed for the direct conversion of a ruthenium refinery salt from Refinery A to $[RuCl_2(COD)]_x$ was about 97%, which was obtained under the following conditions: 3 eq. $FeCl_2*4H_2O$, 1-butanol solvent, 115° C., 24 hours. The $[RuCl_2(COD)]_x$ product obtained in this manner was found to contain between about 1% and about 3% Fe contamination.

In the case of a ruthenium refinery salt obtained from Refinery B, removal of excess $NH_4Cl$ (e.g., by alcohol wash or, more preferably, by water wash) was required prior to attempting the reaction of the ruthenium refinery salt with an L-type ligand (e.g., cyclooctadiene) and reducing agent (e.g., $FeCl_2*4H_2O$). As described above, the conversion does not proceed in the absence of an added reducing agent (Scheme 2, top). The best yield observed for the direct conversion of a purified (i.e., by water wash) ruthenium refinery salt from Refinery B to $[RuCl_2(COD)]_x$ was about 98%, which was obtained under the following conditions: 3 eq. $FeCl_2*4H_2O$, ethanol solvent, 85° C., 24 hours. The $[RuCl_2(COD)]_x$ product obtained in this manner was found to contain between about 2% and about 3% Fe contamination.

Figure 3:
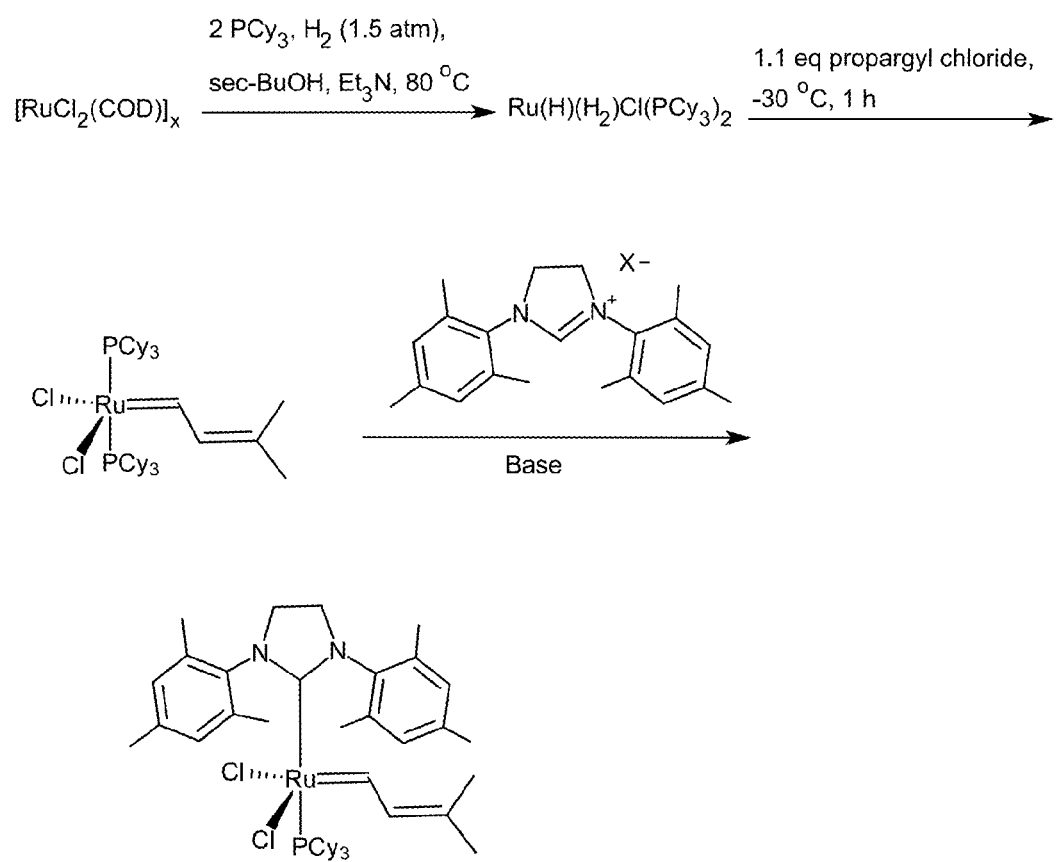
FIG. 3 shows a representative synthetic scheme for converting the ruthenium carbene complex precursor [RuCl$_2$(COD)]$_x$ to a ruthenium carbene compound for use as an olefin metathesis catalyst.

In some embodiments, as shown in FIG. 3, a method for preparing a ruthenium vinylcarbene complex comprises converting a ruthenium carbene complex precursor prepared in accordance with the present teachings into a ruthenium hydrido halide complex, and reacting the ruthenium hydrido halide complex with a propargyl halide to form the ruthenium vinylcarbene complex. In some embodiments, the vinylcarbene complex constitutes a first-generation Grubbs-type olefin metathesis catalyst. In some embodiments, as shown in FIG. 3, the converting of the ruthenium carbene complex precursor into the ruthenium hydrido halide complex comprises reacting the ruthenium carbene complex precursor with a trialkyl phosphine, hydrogen, and a trialkyl amine as described, for example, in *Organometallics*, 1997, 16, No. 18, 3867-3869.

In some embodiments, the ruthenium hydrido halide complex comprises a compound having a structure $[Ru(H)(H_2)X(PR^1R^2R^3)_2]$, wherein X is a halide and wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. In some embodiments, covalent bonds may optionally exist between two or more of $R^1$, $R^2$, and $R^3$. In some embodiments, two of $R^1$, $R^2$, and $R^3$ taken together may optionally form a ring with phosphorus. In some embodiments, the $C_1$-$C_{10}$ alkyl group is primary alkyl, secondary alkyl or cycloalkyl. In some embodiments, the cycloalkyl is cyclohexyl (Cy). In some embodiments, the ruthenium hydrido halide complex comprises a compound having a structure $[Ru(H)(H_2)Cl(PCy_3)_2]$. In some embodiments, the propargyl halide comprises 3-chloro-3-methyl-1-butyne. In some embodiments, as shown in FIG. 3, the ruthenium vinylcarbene complex prepared from the ruthenium carbene complex precursor comprises a compound having a structure $(PCy_3)_2Cl_2Ru=CH-CH=C(CH_3)_2$.

In some embodiments, the above-described method for preparing a ruthenium vinylcarbene complex further comprises replacing a phosphorus-containing ligand of the ruthenium vinylcarbene complex $[Ru(H)(H_2)X(PR^1R^2R^3)_2]$ with an N-heterocyclic carbene ligand as described, for example, in U.S. Pat. No. 7,329,758 B1. In some embodiments, a phosphorus-containing ligand of the ruthenium vinylcarbene complex (e.g., a trialkyl phosphine ligand) is replaced with an imidazolidine ligand to form an imidazolidine-containing ruthenium vinylcarbene complex. In some embodiments, as shown in FIG. 3, the imidazolidine ligand comprises 1,3-dimesityl-4,5-dihydroimidazole. In some embodiments, the imidazolidine-containing ruthenium vinylcarbene complex constitutes a second-generation Grubbs-type olefin metathesis catalyst.

Figure 5:
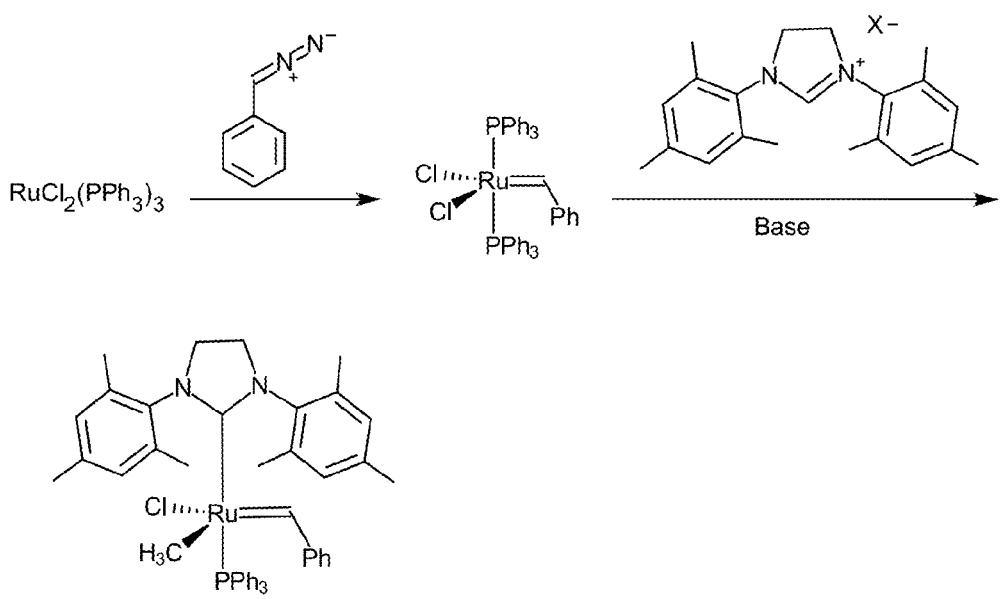
FIG. 5 shows a representative synthetic scheme for converting the ruthenium carbene complex precursor RuCl$_2$(PPh$_3$)$_3$ to a ruthenium carbene compound for use as an olefin metathesis catalyst.

In some embodiments, as shown in FIG. 5, a method for preparing a ruthenium carbene complex comprises converting a ruthenium carbene complex precursor prepared in accordance with the present teachings into a ruthenium carbene complex having a structure $(PR^1R^2R^3)_2Cl_2Ru=CH-R^4$, wherein $R^1$, $R^2$, $R^3$, and $R^4$ are alike or different, and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof. In some embodiments, covalent bonds may optionally exist between two or more of $R^1$, $R^2$, and $R^3$. In some embodiments, two of $R^1$, $R^2$, and $R^3$ taken together may optionally form a ring with phosphorus. In some embodiments, one or more of $R^1$, $R^2$, $R^3$, and $R^4$ comprises phenyl. In some embodiments, each of $R^1$, $R^2$, $R^3$, and $R^4$ comprises phenyl. In some embodiments, one or more of $R^1$, $R^2$, $R^3$, and $R^4$ comprises cycloalkyl (e.g., cyclohexyl). In some embodiments, each of $R^1$, $R^2$, $R^3$, and $R^4$ comprises cycloalkyl (e.g., cyclohexyl). In some embodiments, the carbene complex constitutes a first-generation Grubbs-type olefin metathesis catalyst. In some embodiments, as shown in FIG. 5, the converting of the ruthenium carbene complex precursor into a ruthenium carbene complex comprises reacting the ruthenium carbene complex precursor with phenyldiazomethane as described, for example, in *J. Am. Chem. Soc.*, 1996, 118, 100.

In some embodiments, as shown in FIG. 5, the above-described method for preparing a ruthenium carbene complex further comprises replacing a phosphorus-containing ligand of the ruthenium carbene complex (e.g., a phosphine) with an N-heterocyclic carbene ligand to form an N-heterocyclic carbene-containing ruthenium carbene complex. In some embodiments, a phosphorus-containing ligand of the ruthenium carbene complex is replaced with an imidazolidine ligand to form an imidazolidine-containing ruthenium carbene complex. In some embodiments, as shown in FIG. 5, the imidazolidine ligand comprises 1,3-dimesityl-4,5-dihydroimidazole. In some embodiments, the imidazolidine-containing ruthenium carbene complex constitutes a second-generation Grubbs-type olefin metathesis catalyst.

By way of illustration, as shown in FIGS. 3 and 5, ruthenium carbene complex precursors such as $[RuCl_2(COD)]_x$ and $RuCl_2(PPh_3)_3$ prepared in accordance with the present teachings can be readily transformed into ruthenium carbene complexes for use as olefin metathesis catalysts (e.g., first- and/or second-generation Grubbs-type metathesis catalysts). Moreover, in contrast to conventional methodology, the present teachings circumvent costly conversions of ruthenium refinery salts to ruthenium metal and subsequent oxidation of ruthenium metal to hydrated $RuCl_3$. In addition, the present teachings are in no way limited to the ruthenium feedstock from a particular refinery, and salts from other refineries or sources in addition to the A and B refineries referenced herein may be employed.

The following examples and representative procedures illustrate features in accordance with the present teachings, and are provided solely by way of illustration. They are not intended to limit the scope of the appended claims or their equivalents.

EXAMPLES

Materials

Unless otherwise indicated, all chemicals were used as received and without drying. Ruthenium refinery salt was purchased from Refineries A and B. Ethanol (200 proof, absolute), cis,cis-1,5-cyclooctadiene (>98% pure), $FeCl_2$ (Lot no. MKBJ3791V, catalog ID no. 372870) and $CoCl_2$ (Lot no. BCBG0246V, catalog ID no. 232696) were purchased from Sigma Aldrich. $FeCl_2 * 4H_2O$ (Lot no. 20755900, catalog ID no. 93-2632) was purchased from Strem Chemicals, Inc.

Example 1

XRD Analysis of a First Lot of Ruthenium Refinery Salt from Refinery A

A first lot (lot A) of a Refinery A ruthenium refinery salt was examined by XRD analysis as received. The x-ray powder patterns were measured (Cu $K_\alpha$ radiation, 5-100° 2θ, 0.0202144° steps, 1 sec/step) on a Bruker D2 Phaser diffractometer equipped with a LynxEye position-sensitive detector. Quantitative analysis of the crystalline phases was carried out by the Rietveld method using GSAS.

The lot A ruthenium refinery salt from Refinery A was determined to contain $(NH_4)_4[Ru_2OCl_{10}]$ and 3.9(1) wt % Ru metal impurity. The compound was identified by indexing the pattern on a high-quality body-centered tetragonal unit cell, and using lattice matching techniques to find the K analog (*Acta Cryst. B*, 1979, 35, 558-561). The structure was refined, as shown in Table 2, and hydrogens placed in approximate positions. An acceptable Rietvald refinement was obtained.

TABLE 2

Refined Atom Coordinates of $(NH_4)_4[Cl_5RuORuCl_5]$
Space Group = I 4/m m m
Lattice constants are a = 7.30369(11); b = A; c = 17.0938(4);
Alpha = 90; Beta = 90; Gamma = 90; Cell volume = 911.850(28)

| Name | X | Y | Z | Ui/Ue*100 | Site sym | Mult | Type | Seq | Fractn |
|---|---|---|---|---|---|---|---|---|---|
| Ru1 | 0.000000 | 0.000000 | 0.10779(18) | 2.14 | 4MM(001) | 4 | RU | 1 | 1.0000 |
| Cl2 | 0.22958(28) | 0.22958(28) | 0.11396(26) | 2.12 | M(+−0) | 16 | CL | 2 | 1.0000 |
| Cl3 | 0.000000 | 0.000000 | 0.24535(44) | 2.12 | 4MM(001) | 4 | CL | 3 | 1.0000 |
| O4 | 0.000000 | 0.000000 | 0.000000 | 3.00 | 4/MMM001 | 2 | O | 4 | 1.0000 |
| N5 | 0.000000 | 0.500000 | 0.250000 | 3.00 | −4M2 001 | 4 | N | 5 | 1.0000 |
| N6 | 0.000000 | 0.500000 | 0.000000 | 3.00 | MMM | 4 | N | 6 | 1.0000 |
| H7 | 0.056070 | 0.433980 | 0.216790 | 5.00 | 1 | 32 | H | 7 | 0.5000 |
| H8 | 0.060210 | 0.557780 | 0.029880 | 5.00 | 1 | 32 | H | 8 | 0.5000 |

Example 2

XRD Analysis of Refinery B Ruthenium Refinery Salt

A sample of Refinery B ruthenium refinery salt was first ground with a mortar and pestle prior to analysis but an acceptable powder pattern was not obtained from the damp solid. A portion was ground as an acetone slurry with a mortar and pestle, which resulted in a better powder pattern. The x-ray powder patterns were measured (Cu $K_\alpha$ radiation, 5-100° 2θ, 0.0202144° steps, 1 sec/step) on a Bruker D2 Phaser diffractometer equipped with a LynxEye position-sensitive detector. Quantitative analysis of the crystalline phases was carried out by the Rietveld method using GSAS.

The Refinery B ruthenium refinery salt was determined to contain a mixture of 36.4(2) wt % $(NH_4)_4[Ru_2OCl_{10}]$, 49.6(2) wt % $NH_4Cl$, and 13.9(2) wt % $(NH_4)_2RuCl_5 \cdot H_2O$. The $(NH_4)_4[Ru_2OCl_{10}]$ exhibits significant preferred orientation (texture index=2.02, reflecting difficulty in grinding the large grains to obtain a random powder. The $(NH_4)_2RuCl_5 \cdot H_2O$ was identified by analogy to several $(NH_4)_2RuCl_5X$ compounds. At present, the powder pattern is not yet in the Powder Diffraction File but the crystal structure has been reported (*Zh. Strukt. Khim.*, 2008, 49, 585-588; ICSD collection code 411727). The $(NH_4)_4[Ru_2OCl_{10}]$ in the Refinery B sample exhibits a larger degree of strain broadening than the Refinery A sample.

The phase composition for the Refinery B salt corresponds to a bulk analysis of $C_{0.0}H_{32.51}N_{8.00}O_{0.63}Ru_{1.0}Cl_{11.00}$ compared to the measured $C_{0.09}H_{19.68}N_{5.20}O_{1.30}Ru_{1.0}Cl_{8.43}$. While neither desiring to be bound by any particular theory nor intending to limit in any measure the scope of the appended claims or their equivalents, it is presently believed that the preferred orientation/granularity may have distorted the quantitative analysis and/or that the sample contains some amorphous material.

Example 3

Direct Synthesis of $[RuCl_2(COD)]_x$ from Refinery A Ruthenium Refinery Salt

In a 100-mL, 3-necked flask fitted with an inlet, a condenser, a bubbler, and a stopper, Refinery A ruthenium refinery salt (1.0048 g), cis,cis-1,5-cyclooctadiene (0.80 mL, 2 eq.) and ethanol (25 mL) were refluxed for 24 hours under $N_2$. The solid was not soluble in ethanol; however the color changed from dark brown to lighter brown. The solid was filtered at ambient temperature through a Buchner funnel, and washed with ethanol and acetone. The isolated brown solid was then washed with $H_2O$ (500 mL), yielding a yellow/brown solid $[Cl_2RuCOD]_x$ (0.2632 g; yield=30%).

Example 4

Direct Synthesis of $[RuCl_2(COD)]_x$ from Refinery A Ruthenium Refinery Salt with $FeCl_2$ Reducing Agent In a 100-mL, 3-necked flask fitted with an inlet, a condenser, a bubbler, and a stopper, Refinery A ruthenium refinery salt (1.0093 g), cis,cis-1,5-cyclooctadiene (0.80 mL, 2 eq.), ethanol (25 mL), and $FeCl_2$ (1.2084 g, 3 eq./Ru) were refluxed for 48 hours under $N_2$. The solid was not soluble in ethanol; however the color changed from dark brown to rusty orange. The solid was filtered at ambient temperature through a Buchner funnel, and washed with ethanol and acetone. The isolated rusty orange solid was then washed with $H_2O$ (350 mL), yielding a light rusty orange solid $[Cl_2RuCOD]_x$ (0.7550 g, yield=86%).

Example 5

Direct Synthesis of [RuCl$_2$(COD)]$_x$ from Refinery A Ruthenium Refinery Salt with FeCl*4H$_2$O Reducing Agent In a 100-mL, 3-necked flask fitted with an inlet, a condenser, a bubbler, and a stopper, Refinery A ruthenium refinery salt (1.0092 g), cis,cis-1,5-cyclooctadiene (0.80 mL, 2 eq.), ethanol (30 mL), and FeCl$_2$.4H$_2$O (1.8519 g, 3 eq./Ru) were refluxed for 24 hours under N$_2$. The solid was not soluble in ethanol; however the color changed from dark brown to rusty orange. The solid was filtered at ambient temperature through a Buchner funnel, and washed with ethanol and acetone. The isolated rusty orange solid was then washed with H$_2$O (300 mL), yielding a light rusty orange solid [Cl$_2$RuCOD]$_x$ (0.7235 g, yield=83%).

Example 6

Direct Synthesis of [RuCl$_2$(COD)]$_x$ from Refinery A Ruthenium Refinery Salt with CoCl$_2$*4H$_2$O Reducing Agent In a 100-mL, 3-necked flask fitted with an inlet, a condenser, a bubbler, and a stopper, Refinery A ruthenium refinery salt (0.9923 g), cis,cis-1,5-cyclooctadiene (0.80 mL, 2 eq.), ethanol (30 mL), and CoCl$_2$ (0.8449 g, 2 eq./Ru) were refluxed for 24 hours under N$_2$. The solid was not soluble in ethanol; however the color changed from dark brown to brown. The solid was filtered at ambient temperature through a Buchner funnel, and washed with ethanol and acetone. The isolated brown solid was then washed with H$_2$O (1 L), yielding a yellow/brown solid [Cl$_2$RuCOD]$_x$ (0.5260 g, yield=61%).

Example 7

Attempted Direct Synthesis of [RuCl$_2$(COD)]$_x$ from Refinery B Ruthenium Refinery Salt In a 100-mL, 3-necked flask fitted with an inlet, a condenser, a bubbler, and a stopper, Refinery B ruthenium refinery salt (2.0250 g), cis,cis-1,5-cyclooctadiene (0.80 mL, 2 eq.), and ethanol (25 mL) were refluxed for 24 hours under N$_2$. The solid was not soluble in ethanol; however the color changed from dark brown to red/brown. The solid was filtered at ambient temperature through a Buchner funnel, and washed with ethanol and acetone. The isolated red/brown solid was analyzed by IR and there was no indication of the desired product [Cl$_2$RuCOD]$_x$.

Example 8

Direct Synthesis of [RuCl$_2$(COD)]$_x$ from Refinery B Ruthenium Refinery Salt with FeCl$_2$ Reducing Agent In a 100-mL, 3-necked flask fitted with an inlet, a condenser, a bubbler, and a stopper, Refinery B ruthenium refinery salt (2.0145 g), cis,cis-1,5-cyclooctadiene (0.80 mL, 2 eq.), ethanol (25 mL), and FeCl$_2$ (1.2313 g, 3 eq/Ru) were refluxed for 24 hours under N$_2$. The solid was not soluble in ethanol; however the color changed from dark brown to light brown. The solid was filtered at ambient temperature through a Buchner funnel, and washed with ethanol and acetone. The isolated light brown solid was then washed with H$_2$O (300 mL), yielding a light brown solid [Cl$_2$RuCOD]$_x$ (0.2674 g, yield=30%).

Example 9

Removal of NH$_4$Cl from Refiner B Ruthenium Refiner Salt by Sublimation

In a sublimator, 7.5 g of Refinery B ruthenium salt was sublimed in vacuo (0.05 Torr), at 150-200° C. for 6 hours. NH$_4$Cl sublimes onto the cold finger (−5° C.) (2.2 g) while the Ru salts remain below (4.3 g). Ruthenium salt remaining after sublimation is determined to be (NH$_4$)$_4$[Ru$_2$OCl$_{10}$] and (NH$_4$)$_2$RuCl$_5$.H$_2$O by elemental analysis and IR spectroscopy. Ru wt %=32.9%, up from 18.8% in raw salt.

Example 10

Direct Synthesis of [RuCl$_2$(COD)]$_x$ from Sublimed Refinery B Ruthenium Refinery Salt with FeCl Reducing Agent In a 100-mL, 3-necked flask fitted with an inlet, a condenser, a bubbler, and a stopper, sublimed Refinery B ruthenium refinery salt (1.0028 g), cis,cis-1,5-cyclooctadiene (0.80 mL, 2 eq.), ethanol (25 mL), and FeCl$_2$ (1.0568 g, 3 eq/Ru) were refluxed for 24 hours under N$_2$. The solid was not soluble in ethanol; however the color changed from dark brown to light brown. The solid was filtered at ambient temperature through a Buchner funnel, and washed with ethanol and acetone. The isolated light brown solid was then washed with H$_2$O (500 mL), yielding a light brown solid [Cl$_2$RuCOD]$_x$ (0.0933 g, yield<12%). N.B. The product was still not pure and was contaminated with some starting material.

Example 11

Direct Synthesis of [Cl$_2$RuCOD]$_x$ from Water-Washed Refinery B Ruthenium Refiner Salt with FeCl$_2$ Reducing Agent In a 100-mL Erlenmeyer flask, Refinery B ruthenium refinery salt (10 g) was stirred with H$_2$O (20 mL) for 2 min. The color of the solid changed from black to dark brown. The slurry was then filtered through a Buchner funnel, and washed with water (40 mL) and acetone (10 mL). Purified Refinery B ruthenium refinery salt with the NH$_4$Cl removed was recovered (4.2 g, ruthenium=31.3% by ICP).

In a 100-mL, 3-necked flask fitted with an inlet, a condenser, a bubbler, and a stopper, water-washed Refinery B ruthenium refinery salt (1.9837 g), cis,cis-1,5-cyclooctadiene (1.4 mL, 2 eq.), FeCl$_2$*4H$_2$O (3.2275 g, 2.6 eq.) and ethanol (30 mL) were refluxed under nitrogen for 24 hours. The solid was not soluble in ethanol; however the color changed from dark brown to rusty orange. The solid was filtered hot through a Buchner funnel, and washed with ethanol and acetone. The isolated rusty orange solid was then washed with warm water (100 mL, 70-90° C.), and filtered through a Buchner funnel, yielding a rusty orange solid [Cl$_2$RuCOD]$_x$ (1.71 g, yield=99%).

Example 12

Direct Synthesis of [Cl$_2$RuCOD]$_x$ from Refinery A Ruthenium Refine Salt with FeCl$_2$*4H$_2$O Reducing Agent In a 100-mL, 3-necked flask fitted with an inlet, a condenser, a bubbler, and a stopper, Refinery A ruthenium refinery salt (lot A, 1.0177 g), cis,cis-1,5-cyclooctadiene (0.8 mL, 2 eq.), $FeCl_2*4H_2O$ (1.8609 g, 3 eq.) and 1-butanol (20 mL) were refluxed under nitrogen for 24 hours. The solid was not soluble in butanol; however the color changed from dark brown to rusty orange. The solid was filtered hot through a Buchner funnel, and washed with ethanol and acetone. The isolated rusty orange solid was then washed with warm water (100 mL, 85° C.), and filtered through a Buchner funnel, yielding a rusty orange solid $[RuCl_2(COD)]_x$ (0.8580 g, yield=97%).

In a 100-mL, 3-necked flask fitted with an inlet, a condenser, a bubbler, and a stopper, Refinery A ruthenium refinery salt (lot B, 2.0177 g), cis,cis-1,5-cyclooctadiene (1.6 mL, 2 eq.), $FeCl_2*4H_2O$ (3.7360 g, 3 eq.) and 1-butanol (30 mL) were refluxed under nitrogen for 24 hours. The solid was not soluble in butanol; however the color changed from dark brown to rusty orange. The solid was filtered hot through a Buchner funnel, and washed with ethanol and acetone. The isolated rusty orange solid was then washed with warm water (100 mL, 85° C.), and filtered through a Buchner funnel, yielding a rusty orange solid $[RuCl_2(COD)]_x$ (1.73 g, yield=98%). N.B.: The composition of lot B differed slightly as compared to that of lot A. As further described in Example 18 below, lot B did not contain free Ru metal unlike lot A. In addition, each lot had differing amounts of other contaminates.

Example 13

Direct Synthesis of $[RuCl_2(COD)]_x$ from Water-Washed Refinery B Ruthenium Refinery Salts In a 100-mL Erlenmeyer flask, Refinery B ruthenium refinery salt (10 g) was stirred with $H_2O$ (20 mL) for 2 min. The color of the solid changed from black to dark brown. The slurry was then filtered through a Buchner funnel, and washed with water (40 mL) and acetone (10 mL). Purified Refinery B ruthenium refinery salt (ca. 100% $NH_4Cl$ and $(NH_4)_2RuCl_5*H_2O$ removed) was recovered (4.2 g, ruthenium=31.3% by ICP). About 16% of ruthenium compounds were also removed by water wash.

With $FeCl_2*4H_2O$ Reducing Agent: In a 100-mL, 3-necked flask fitted with an inlet, a condenser, a bubbler, and a stopper, water-washed Refinery B ruthenium refinery salt (1.9837 g), cis,cis-1,5-cyclooctadiene (1.4 mL, 2 eq.), $FeCl_2*4H_2O$ (3.2275 g, 2.6 eq.) and ethanol (30 mL) were refluxed under nitrogen for 24 hours. The solid was not soluble in ethanol; however the color changed from dark brown to rusty orange. The solid was filtered hot through a Buchner funnel, and washed with ethanol and acetone. The isolated rusty orange solid was then washed with warm water (100 mL, 70-90° C.), and filtered through a Buchner funnel yielding a rusty orange solid $[RuCl_2(COD)]_x$ (1.71 g, yield=99%).

Without Reducing Agent: In a 100-mL, 3-necked flask fitted with an inlet, a condenser, a bubbler, and a stopper, water-washed Refinery B ruthenium refinery salt (2.0086 g), cis,cis-1,5-cyclooctadiene (1.4 mL, 2 eq.), and ethanol (30 mL) were refluxed under nitrogen for 26 hours. The solid was not soluble in ethanol; however the color changed from dark brown to rusty orange. The solid was filtered hot through a Buchner funnel, and washed with ethanol and acetone. The isolated rusty orange solid was then washed with warm water (250 mL, 70-90° C.), and filtered through a Buchner funnel yielding a rusty orange solid $[RuCl_2(COD)]_x$ (0.9357 g, yield=54%).

Example 14

Direct Synthesis of $[RuCl_2(COD)]_x$ from Ethanol-Washed Refinery B Ruthenium Refiner Salts with $FeCl_2*4H_2O$ Reducing Agent In a 250-mL, round-bottomed flask fitted with a condenser, Refinery B ruthenium refinery salt (5.1 g) and ethanol (300 mL) were refluxed for 2.5 hours. The slurry was filtered hot through a Buchner funnel, then returned to the round-bottomed flask and heated with additional ethanol (200 mL) for 1 hr. The slurry was filtered hot through a Buchner funnel. Ethanol-washed Refinery B ruthenium refinery salt was recovered (2.9 g, ca. 86% of $NH_4Cl$ removed).

In a 100-mL, 3-necked flask fitted with an inlet, a condenser, a bubbler, and a stopper, ethanol-washed Refinery B ruthenium refinery salt (1.9938 g), cis,cis-1,5-cyclooctadiene (1.3 mL, 2 eq.), $FeCl_2*4H_2O$ (3.2057 g, 3 eq.) and ethanol (30 mL) were refluxed under nitrogen for 24 hours. The solid was not soluble in ethanol; however the color changed from dark brown to rusty orange. The solid was filtered hot through a Buchner funnel, and washed with ethanol and acetone. The isolated rusty orange solid was then washed with warm water (150 mL, 70-90° C.), and filtered through a Buchner funnel yielding a rusty orange solid $[RuCl_2(COD)]_x$ (1.2218 g, yield=79%).

Example 15

Direct Synthesis of $[RuCl_2(COD)]_x$ from Ethanol-Extracted Refinery B Ruthenium Refinery Salts with $FeCl_2*4H_2O$ Reducing Agent The glass thimble of a Soxhlet extractor was filled with Refinery B ruthenium refinery salt (25.05 g), and the reservoir was filled with ethanol (150 mL). The extractor was heated to 125° C. for 13 total hours. The remaining solid was then removed from the thimble and dried at 85° C. Purified Refinery B ruthenium refinery salt was recovered (15.0 g, ca. 80% $NH_4Cl$ removed).

In a 100-mL, 3-necked flask fitted with an inlet, a condenser, a bubbler, and a stopper, ethanol-extracted Refinery B ruthenium refinery salt (2.0055 g), cis,cis-1,5-cyclooctadiene (1.4 mL, 2 eq.), $FeCl_2*4H_2O$ (3.2150 g, 3 eq.) and ethanol (40 mL) were refluxed under nitrogen for 24 hours. The solid was not soluble in ethanol; however the color changed from dark brown to rusty orange. The solid was filtered hot through a Buchner funnel, and washed with ethanol and acetone. The isolated rusty orange solid was then washed with warm water (150 mL, 70-90° C.), and filtered through a Buchner funnel yielding a rusty orange solid $[RuCl_2(COD)]_x$ (0.4871 g, yield=32%).

Example 16

Purification of Refinery B Ruthenium Refinery Salts Via Butanol Extraction

The glass thimble of a Soxhlet extractor was filled with Refinery B ruthenium refinery salt (20.0132 g), and the reservoir was filled with butanol (150 mL). The extractor was heated to 145° C. for 14 total hours. The remaining solid was then removed from the thimble and dried at 115° C.

Purified Refinery B ruthenium refinery salt was recovered (17.65 g, ca. 24% NH$_4$Cl removed).

Example 17

Effect of Solvent Boiling Point on Yield of [RuCl2(COD)]$_x$ Prepared Via Direct Conversion of a Refinery A Ruthenium Refinery Salt Ethanol as solvent: In a 100-mL, 3-necked flask fitted with an inlet, a condenser, a bubbler, and a stopper, Refinery A ruthenium refinery salt (1.0092 g), cis,cis-1,5-cyclooctadiene (0.80 mL, 2 eq.), ethanol (30 mL), and FeCl$_2$*4H$_2$O (1.8519 g, 3 eq./Ru) were refluxed for 24 hours under N$_2$. The solid was not soluble in ethanol; however the color changed from dark brown to rusty orange. The solid was filtered at ambient temperature through a Buchner funnel, and washed with ethanol and acetone. The isolated rusty orange solid was then washed with H$_2$O (300 mL), yielding a light rusty orange solid [RuCl$_2$(COD)]$_x$ (0.7235 g, yield=83%).

1-Butanol as solvent: In a 100-mL, 3-necked flask fitted with an inlet, a condenser, a bubbler, and a stopper, Refinery A ruthenium refinery salt (1.0177 g), cis,cis-1,5-cyclooctadiene (0.80 mL, 2 eq.), 1-butanol (30 mL), and FeCl$_2$.4H$_2$O (1.88609 g, 3 eq./Ru) were refluxed for 24 hours under N$_2$. The solid was not soluble in ethanol; however the color changed from dark brown to rusty orange. The solid was filtered at ambient temperature through a Buchner funnel, and washed with ethanol and acetone. The isolated rusty orange solid was then washed with H$_2$O (150 mL), yielding a light rusty orange solid [RuCl$_2$(COD)]$_x$ (0.8580 g, yield=97%).

Example 18

XRD Analysis of Additional Ruthenium Refinery Salts

The following four ammonium ruthenium chloride samples were examined by XRD analysis, as summarized in Table 3 below: (1) a lot B sample from Refinery A; (2) a lot C sample from Refinery A; (3) a first water-washed sample from Refinery B (54% recovered); and (4) a second water-washed sample from Refinery B (44% recovered). Of these, samples (1) and (2) were examined as received, while samples (3) and (4) were ground with a mortar and pestle.

The x-ray powder patterns were measured (Cu K$_\alpha$ radiation, 5-100° 2θ, 0.0202144° steps, 0.5 sec/step) on a Bruker D2 Phaser diffractometer equipped with a LynxEye position-sensitive detector. Analysis of the crystalline phases was carried out by the Rietveld method using GSAS.

All four samples are highly crystalline. Three of the samples—(1), (2), and (4)—are phase pure, while sample (3) contains small concentrations of (NH$_4$)$_2$RuCl$_5$.H$_2$O and NH$_4$Cl. No Ru metal was detected in any of the samples. All four samples contain large (>3000 Å) crystallites of (NH$_4$)$_4$[Ru$_2$OCl$_{10}$]. Visually, the crystallites of the two Refinery B samples—viz., samples (3) and (4)—were larger even after grinding with a mortar and pestle. All four patterns exhibit significant preferred orientation, consistent with the expected {001} platy morphology expected for this phase. The lattice parameters of the (NH$_4$)$_4$[Ru$_2$OCl$_{10}$] from the two different refineries differ slightly but significantly from one another. The peak profiles contain small strain broadening contributions, which differ between the samples from the two refineries.

TABLE 3

XRD Data for Four Additional Samples of Ruthenium Refinery Salts

| | Sample (1) Refinery A (lot B) | Sample (2) Refinery A (lot C) | Sample (3) Water-Washed Refinery B (54% recovered) | Sample (4) Water-Washed Refinery B (44% recovered) |
|---|---|---|---|---|
| (NH$_4$)$_4$[Ru$_2$OCl$_{10}$] (wt %) | 100 | 100 | 91.7(1) | 100 |
| a, Å | 7.3165(2) | 7.3184(1) | 7.3196(2) | 7.3212(1) |
| c, Å | 17.0751(3) | 17.0694(3) | 17.0837(2) | 17.0850(2) |
| V, Å$^3$ | 914.04(5) | 914.23(4) | 915.28(6) | 915.76(4) |
| Profile Y | 9.9(6) | 10.2(4) | 6.1(9) | 5.7(5) |
| stec(001) | −4.5(7) | −4.5(6) | −5.1(9) | −1.3(6) |
| Texture Index | 1.73 | 1.19 | 3.57 | 1.85 |
| Ru (wt %) | 0 | 0 | 0 | 0 |
| (NH$_4$)$_2$RuCl$_5$•H$_2$O (wt %) | — | — | 6.4(2) | — |
| NH$_4$Cl (wt %) | — | — | 2.0(2) | — |

Example 19

Direct Conversion of Water Washed Refinery B Ruthenium Refinery Salts to [Cl$_2$RuCOD]$_x$ (100-Gram Scale)

Ethanol (1 L) was added to a two-liter, three-necked round-bottom flask fitted to an overhead stirrer. The overhead stirrer was turned on low, and the water-washed ruthenium refinery salt (100.00 g), FeCl$_2$.4H$_2$O (165.18 g), and 1,5-cyclo-octadiene (59.92 g) were added slowly. Ethanol (1 L) was added, a condenser (5° C.) was attached to the left neck, and a nitrogen inlet was attached to the right neck. The reaction refluxed under N$_2$, with aggressive stirring, at 85° C., over a period of 24 hours. The product was filtered warm through a Buchner funnel and washed with ethanol (450 mL) and acetone (300 mL). The solid filtrate was collected and stirred aggressively with water (2 L) at 85° C. for 1.75 hours. The mixture was filtered warm through a Buchner funnel, washed with water (1 L), and washed with acetone (400 mL). The solid was collected and dried thoroughly, yielding 75.92 g (97.9%) [Cl$_2$RuCOD]$_x$.

Example 20

Direct Conversion of Refinery A Ruthenium Refinery Salts to [Cl$_2$RuCOD]$_x$ (100-Gram Scale)

Butanol (1 L) was added to a two liter, three-necked round-bottom flask fitted to an overhead stirrer. The overhead stirrer was turned on low, and the Refinery A ruthenium refinery salt (100.00 g), FeCl$_2$.4H$_2$O (123.33 g), and 1,5-cyclooctadiene (67.11 g) were added slowly. Butanol (1 L) was added, a condenser (5° C.) was attached to the left neck, and a nitrogen inlet was attached to the right neck. The reaction refluxed under N$_2$, with aggressive stirring, at 115° C., over a period of 24 hours. The product was filtered warm through a Buchner funnel and washed with ethanol (1.5 L) and acetone (850 mL). The solid filtrate was collected and stirred aggressively with water (2 L) at 85° C. for an hour. The mixture was filtered warm through a Buchner funnel, washed with water (1 L), and washed with acetone (400 mL). The solid filtrate was collected and stirred aggressively with water (2 L) at 85° C. for an hour. The mixture was filtered warm through a Buchner funnel, washed with water (500 mL), and washed with acetone (500 mL). The solid was collected and dried thoroughly, yielding 84.80 g (97.6%) [Cl$_2$RuCOD]$_x$.

Example 21

Synthesis of (PCy$_3$)$_2$Cl$_2$Ru(=CH—CH=CMe$_2$) from Synthesized [Cl$_2$RuCOD]$_x$ In-house synthesized [Cl$_2$RuCOD]$_x$ (1.003 g) and tricyclohexylphosphine (PCy$_3$, 2.076 g) were loaded into a 3-oz. Fisher Porter (F-P) bottle in the glovebox. The flask was sealed with a valve, removed from the glovebox, and attached to a nitrogen-hydrogen gas manifold. After purging with N$_2$, 2-butanol (40 mL, sparged with N$_2$ for 20 min.) and triethylamine (0.5 mL) were added by syringe. The system was then purged with H$_2$, the system pressurized to 25 psig H$_2$, and the reaction heated to 80° C. with vigorous stirring for 7 hours repressurizing as needed. The reaction changed color slightly from rusty orange to lighter orange. The reaction was cooled, then stirred overnight at room temperature under 10 psig H$_2$. The next day, the system was cooled to 0° C. in an ice bath, the F-P bottle was purged with N$_2$, then 3-chloro-3-methyl-1-butyne (0.6 mL, filtered through a silica plug) was added dropwise by gas-tight syringe under flowing N$_2$. The reaction was stirred at 0° C. for 2 hours then at room temperature for 2 hours under atmospheric N$_2$ venting occasionally to remove evolved H$_2$. The slurry changed from orange to a dark rose purple. Methanol (30 mL) was added in air, and the slurry was stirred for 5 min to precipitate as much product as possible. The slurry was vacuum filtered through a Buchner funnel and the resulting solid was washed with 20 mL methanol, dried in vacuo for 2 hours, then stored in the glovebox. Yield=2.14 g (PCy$_3$)$_2$Cl$_2$Ru(=CH—CH=CMe$_2$); 74.8% rose purple solid.

Example 22

Synthesis of (PCy$_3$)$_2$Cl$_2$Ru(=CH—CH=CMe$_2$) from Commercial [Cl$_2$RuCOD]$_x$ Commercial [Cl$_2$RuCOD]$_x$ (Strem, 1.011 g) and tricyclehexylphosphine (PCy$_3$, 2.046 g) were loaded into a 3-oz. Fisher Porter (F-P) bottle in the glovebox. The flask was sealed with a valve, removed from the glovebox, and attached to a nitrogen-hydrogen gas manifold. After purging with N$_2$, 2-butanol (40 mL, sparged with N$_2$ for 20 min) and triethylamine (0.5 mL) were added by syringe. The system was then purged with H$_2$, the system pressurized to 25 psig H$_2$, and the reaction heated to 80° C. with vigorous stirring for 7 hours repressurizing as needed. The reaction solution changed from clear with black solid to yellow then orange then milky dark orange, and the undissolved [Cl$_2$RuCOD]$_x$ disappeared as the reaction proceeded. The reaction was cooled, then stirred overnight at room temperature under 10 psig H$_2$. The next day, the system was cooled to 0° C. in an ice bath, the F-P bottle was purged with N$_2$, then 3-chloro-3-methyl-1-butyne (0.6 mL, filtered through a silica plug) was added dropwise by gastight syringe under flowing N$_2$. The reaction was stirred at 0° C. for 2 hours then at room temperature for 2 hours under atmospheric N$_2$ venting occasionally to remove evolved H$_2$. The slurry changes from orange to a dark rose purple. Methanol (30 mL) was added in air, and the slurry was stirred for 5 min to precipitate as much product as possible. The slurry was vacuum filtered through a Buchner funnel and the resulting solid was washed with 20 mL methanol, dried in vacuo for 2 hours, then stored in the glovebox. Yield=1.99 g (PCy$_3$)$_2$Cl$_2$Ru(=CH—CH=CMe$_2$); 68.9% rose purple solid.

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A method for preparing a ruthenium carbene complex precursor comprising:
   reacting a ruthenium refinery salt with an L-type ligand and a reducing agent to form the ruthenium carbene complex precursor, the ruthenium refinery salt being an ammonium salt of a halogen-containing ruthenium complex, wherein the halogen-containing ruthenium complex comprises chlorine.

2. The method of claim 1, wherein the L-type ligand is an olefin, a phosphine, a phosphite, an amine, CO, N$_2$, or a combination thereof.

3. The method of claim 2, wherein the L-type ligand comprises a cyclic olefin.

4. The method of claim 3, wherein the cyclic olefin is cyclohexadiene, cycloheptadiene, cyclooctadiene, cyclononadiene, cyclodecadiene, cycloundecadiene, cyclododecadiene, cyclododecatriene, paramenthadiene, phellandrene, norbornadiene, terpinene, limonene, or a combination thereof.

5. The method of claim 3, wherein the cyclic olefin comprises cyclooctadiene.

6. The method of claim 2, wherein the L-type ligand comprises a phosphorus-containing ligand having a structure $PR^1R^2R^3$;
wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof; and
wherein covalent bonds may optionally exist between two or more of $R^1$, $R^2$, and $R^3$; and
wherein any two of $R^1$, $R^2$, and $R^3$ taken together may optionally form a ring with the phosphorus atom.

7. The method of claim 6 wherein the phosphorus-containing ligand comprises triphenyl phosphine.

8. The method of claim 1, wherein the ruthenium refinery salt comprises $(NH_4)_2RuCl_5$, $(NH_4)_2RuCl_5 \cdot H_2O$, polyhydrated $(NH_4)_2RuCl_5$, $(NH_4)_4[Ru_2OCl_{10}]$, or a combination thereof.

9. The method of claim 8, wherein the ruthenium refinery salt further comprises $NH_4Cl$.

10. The method of claim 9, wherein the method further comprises removing at least a portion of the $NH_4Cl$ from the ruthenium refinery salt prior to the reacting.

11. The method of claim 1, wherein the reducing agent comprises a metal selected from the group consisting of Group 7 elements, Group 8 elements, Group 9 elements, Group 10 elements, Group 11 elements, and combinations thereof.

12. The method of claim 11, wherein the reducing agent comprises $FeCl_2$ or a hydrated form thereof.

13. The method of claim 11 wherein the reducing agent comprises $CoCl_2$ or a hydrated form thereof.

14. The method of claim 1, wherein the reducing agent is present at a loading of at least about 1 molar equivalent relative to ruthenium in the ruthenium refinery salt.

15. The method of claim 1, wherein the reacting of the ruthenium refinery salt with the L-type ligand and the reducing agent is performed in an alcoholic solvent.

16. The method of claim 1, wherein the reacting of the ruthenium intermediate with the L-type ligand and the reducing agent comprises a reaction time of at least about 5 hours.

17. The method of claim 1, wherein the ruthenium carbene complex precursor comprises a material having a structure $[RuCl_2(COD)]_x$, wherein x is an integer value of 1 or more.

18. The method of claim 1, wherein the ruthenium carbene complex precursor comprises a material having a structure $RuCl_2(PR^1R^2R^3)_3$;
wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof; and
wherein covalent bonds may optionally exist between two or more of $R^1$, $R^2$, and $R^3$; and
wherein any two of $R^1$, $R^2$, and $R^3$ taken together may optionally form a ring with the phosphorus atom.

19. The method of claim 1, wherein the reacting of the ruthenium refinery salt with the L-type ligand and the reducing agent is performed in a non-reactive solvent or in a solvent mixture that comprises one or a plurality of non-reactive solvents.

20. The method of claim 19, wherein the solvent mixture further comprises one or a plurality of alcohols.

21. The method of claim 19, wherein the non-reactive solvent comprises an alkane.

22. A method for preparing a ruthenium carbene complex precursor comprising:
reacting a ruthenium refinery salt with an L-type ligand and a reducing agent to form the ruthenium carbene complex precursor;
wherein the L-type ligand comprises cyclooctadiene or a phosphorus-containing material having a structure $PR^1R^2R^3$;
wherein the ruthenium refinery salt comprises a material selected from the group consisting of $(NH_4)_2RuCl_5$, $(NH_4)_2RuCl_5 \cdot H_2O$, polyhydrated $(NH_4)_2RuCl_5$, $(NH_4)_4[Ru_2OCl_{10}]$, and combinations thereof;
wherein the reducing agent comprises a metal selected from the group consisting of Group 7 elements, Group 8 elements, Group 9 elements, Group 10 elements, Group 11 elements, and combinations thereof;
wherein the ruthenium carbene complex precursor comprises a compound having a structure $[RuCl_2(COD)]_x$ or a compound having a structure $RuCl_2(PR^1R^2R^3)_3$;
wherein x is an integer value of 1 or more;
wherein $R^1$, $R^2$, and $R^3$ are alike or different and are each independently selected from the group consisting of substituted or unsubstituted aryl, substituted or unsubstituted $C_1$-$C_{10}$ alkyl, substituted or unsubstituted aryloxy, substituted or unsubstituted $C_1$-$C_{10}$ alkoxy, and combinations thereof; and
wherein covalent bonds may optionally exist between two or more of $R^1$, $R^2$, and $R^3$; and
wherein any two of $R^1$, $R^2$, and $R^3$ taken together may optionally form a ring with phosphorus.

23. The method of claim 22, wherein the reducing agent is selected from the group consisting of $FeCl_2$, $CoCl_2$, hydrated forms thereof, and combinations thereof.

24. A method of preparing a product that comprises $[RuCl_2(COD)]_x$, the method comprising:
reacting a ruthenium refinery salt with cyclooctadiene and a reducing agent in an alcoholic solvent under reflux conditions to form the product;
wherein x is an integer value of 1 or more;
wherein the ruthenium refinery salt comprises a material selected from the group consisting of $(NH_4)_2RuCl_5$, $(NH_4)_2RuCl_5 \cdot H_2O$, polyhydrated $(NH_4)_2RuCl_5$, $(NH_4)_4[Ru_2OCl_{10}]$, and combinations thereof; and
wherein the reducing agent comprises a metal selected from the group consisting of Group 7 elements, Group 8 elements, Group 9 elements, Group 10 elements, Group 11 elements, and combinations thereof.

* * * * *